United States Patent [19]

Goddard et al.

[11] Patent Number: 4,994,628

[45] Date of Patent: Feb. 19, 1991

[54] PHENOLIC ANTIOXIDANT PROCESS

[75] Inventors: Lloyd E. Goddard; George L. Mina, both of Orangeburg, S.C.

[73] Assignee: Ethyl Corporation, Richmond, Va.

[21] Appl. No.: 411,631

[22] Filed: Sep. 25, 1989

[51] Int. Cl.$^5$ .............................................. C07C 39/12
[52] U.S. Cl. .................................... 568/720; 568/717; 568/718; 568/719
[58] Field of Search ............... 568/717, 718, 719, 720, 568/913

[56] References Cited

U.S. PATENT DOCUMENTS

| | | | |
|---|---|---|---|
| 3,644,536 | 2/1972 | Starnes | 568/720 |
| 3,925,488 | 12/1975 | Shin | 568/720 |
| 4,259,534 | 3/1981 | Gurvich et al. | 568/720 |
| 4,415,409 | 11/1983 | Zudkevitch et al. | 568/913 |
| 4,870,214 | 9/1989 | Mina et al. | 568/720 |
| 4,898,994 | 2/1990 | Livingston | 568/720 |

FOREIGN PATENT DOCUMENTS

| | | | |
|---|---|---|---|
| 44-92237 | 7/1981 | Japan | 568/720 |
| 197708 | 9/1977 | U.S.S.R. | 568/913 |

Primary Examiner—Werren B. Lone
Attorney, Agent, or Firm—Joseph D. Odenweller; Patricia J. Hogan

[57] ABSTRACT 3,5-dialkyl-4-hydroxybenzyl-substituted benzene compounds are made by reacting 2,6-dialkyl-4-methoxymethyl phenols with a benzene compound having an unsubstituted nuclear position in an inert solvent and in the presence of sulfuric acid catalyst while distilling methanol by-product from the reaction mixture as it forms.

19 Claims, No Drawings

PHENOLIC ANTIOXIDANT PROCESS

BACKGROUND

Rocklin et al. U.S. Pat. No. 3,026,264 describes the antioxidant use of several 3,5-dialkyl-4-hydroxybenzyl-substituted benzenes such as 2,4,6-tri(3,5-di-tert-butyl-4-hydroxybenzyl)mesitylene. They are made by the reaction of 2,6-dialkyl-4-hydroxymethyl phenots with a benzene compound in an inert solvent at −15 to 100° C. in the presence of sulfuric acid or a Friedel Crafts catalyst.

Gurvich et al. G.B. No. 1,327,542 discloses a process for making 2,4,6-tri(3,5-dialkyl-4-hydroxybenzyl)benzenes by reacting a 2,6-dialkyl-4-methoxymethyl phenol with an alkylbenzene compound in an inert solvent in the presence of an acidic catalyst such as sulfuric acid. In Examples 1, 3, and 4, Gurvich et al. uses 364 parts by weight 94% sulfuric acid per mole part mesitylene. In a commercial operation this presents a severe spent sulfuric acid disposal problem. However, merely reducing the amount of sulfuric acid results in a reaction wherein less than all of the reactive positions on the benzene compound become substituted. In the case of mesitylene and 2,6-di-tert-butyl-4-methoxymethyl phenol, lowering the amount of sulfuric acid gives a product which contains both mono- and di-3,5-di-tert-butyl-4-hydroxybenzyl-substituted mesitylene by-products, making it unacceptable for commercial sale. Thus, a need exists for a process which allows reduction in the amount of sulfuric acid used as catalyst and at the same time gives a product suitable for commercial use.

SUMMARY

It has now been discovered that the reaction of a 2,6-dialkyl-4-methoxymethyl phenol with a benzene compound such as mesitylene can be effectively catalyzed using reduced amounts of sulfuric acid by conducting the reaction under temperature and pressure conditions that cause the methanol formed during the reaction to distill out of the reaction mixture.

DESCRIPTION OF THE PREFERRED EMBODIMENTS

A preferred embodiment of the invention is a process for making a compound having the structure:

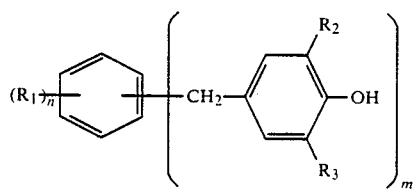

by reacting a reactant having the structure:

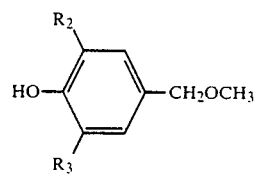

with a benzene compound having the structure:

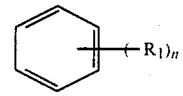

wherein $R_1$ is a $C_{1-3}$ lower alkyl and $R_2$ and $R_3$ are independently selected from the group consisting of $C_{1-8}$ alkyl, $C_{5-8}$ cycloalkyl and $C_{7-12}$ aralkyl, n is zero or an integer from 1 to 4, m is an integer from 2 to 3, and m+n does not exceed 6, in an inert solvent in the presence of sulfuric acid at a temperature of about 20°–150° C. and at a pressure such that methanol by-product formed in the reaction distills out of the reaction mixture as it is formed.

In describing the present invention, the word "alkyl" in 2,6-dialkyl-4-methoxymethyl phenol includes cycloalkyls and arylalkyls and the two alkyls on each such reactant can be the same or different.

Useful 2,6-dialkyl-4-methoxymethyl phenols include:
2,6-dimethyl-4-methoxymethyl phenol
2-methyl-6-tert-butyl-4-methoxymethyl phenol
2,6-diisopropyl-4-methoxymethyl phenol
2,6-diisobutyl-4-methoxymethyl phenol
2,6-di-tert-butyl-4-methoxymethyl phenol
2,6-di-sec-butyl-4-methoxymethyl phenol
2-methyl-6-tert-octyl-4-methoxymethyl phenol
2-methyl-6-cyclopentyl-4-methoxymethyl phenol
2,6-dicyclopentyl-4-methoxymethyl phenol
2,6-dicyclohexyl-4-methoxymethyl phenol
2-tert-butyl-6-cyclooctyl-4-methoxymethyl phenol
2,6-dibenzyl-4-methoxymethyl phenol
2-methyl-6-benzyl-4-methoxymethyl phenol
2,6-di-($\alpha$-methylbenzyl)-4-methoxymethyl phenol
2-methyl-6-($\alpha$-methylbenzyl)-4-methoxymethyl phenol
2-isopropyl-6-($\alpha,\alpha$-dimethylbenzyl)-4-methoxymethyl phenol.

The most preferred 2,6-dialkyl-4-methoxymethyl phenol is 2,6-di-tert-butyl-4-methoxymethyl phenol.

Suitable benzene compounds include benzene and $C_{1-3}$ alkyl-substituted benzenes such as toluene, m-xylene, p-xylene, durene, mesitylene, ethylbenzene, 1,3-diethylbenzene, 1,4-diisopropylbenzene and the like. The preferred benzene compounds are the methyl-substituted benzenes such as durene and especially mesitylene.

Useful solvents include any normally liquid material that is substantially inert under reaction conditions. Such solvents include aliphatic and cycloaliphatic hydrocarbons as well as aliphatic and aromatic halohydrocarbons. Representative examples are cyclohexane, heptane, octane, isooctane, nonane, dichloromethane, chloroform, carbon tetrachloride, 1,2-dichloroethane, dibromoethane and the like.

The most preferred inert solvents are the normally liquid aliphatic and aromatic halohydrocarbons boiling in the range of 40°–200° C. More preferably the halohydrocarbon will boil in the range of 50°–150° C. at atmospheric pressure. Representative examples of such solvents are 1,2-dichloroethane, 1,1-dichloroethane, 1,1,1-trichloroethane, 1,1,2-trichloroethane, 1,1,2-trichloropropane, 1,1,2,2-tetrachloroethane, dibromomethane, chlorobenzene, chloroform, carbon tetrachloride 1,1-dibromoethane, 1,2-dibromoethane, 1,1,1,2-tetrachloroethane and the like. The most preferred solvent is 1,1,1-trichloroethane.

The amount of solvent should be a solvent amount. This is an amount that will hold the 2,6-dialkyl-4-methoxymethyl phenol and benzene compound in solution. A useful range is about 500-1000 parts by weight inert solvent per each 100 parts of total benzene compound plus 2,6-dialkyl-4-methoxymethyl phenol. In a more preferred embodiment, only part of the solvent (e.g., 25-50 weight percent) is placed in the reaction vessel together with the benzene compound and sulfuric acid. The remainder is used to dissolve the 2,6-dialkyl-4-methoxymethyl phenol being added to the reactor.

The mole ratio of 2,6-dialkyl-4-methoxymethyl phenol to benzene compounds depends on the number of 3,5-dialkyl-4-hydroxybenzyl groups to be introduced into the benzene compound. The moles of 2,6-dialkyl-4-methoxymethyl phenol should be 100-130% of the stoichiometric amount. With durene the stoichiometric amount is 2 moles per mole of durene and with mesitylene the stoichiometric amount is 3 moles per mole of mesitylene. A preferred amount is about 110-120% of the stoichiometric amount.

The sulfuric acid used in the process is concentrated $H_2SO_4$. This includes concentrations of about 75-100% and even oleums containing $SO_3$. The more preferred sulfuric acid catalyst is about 80-98 weight percent $H_2SO_4$.

The amount of sulfuric acid is a catalytic amount. The prior art used about 0.9 mole $H_2SO_4$ per mole of 2,6-dialkyl-4-methoxymethyl phenol. The amount of sulfuric acid is expressed in terms of active $H_2SO_4$ content. For example 100 grams of 98 weight percent sulfuric acid is 1.0 gram mole of $H_2SO_4$. The present process permits the use of less sulfuric acid than required by the prior art methods. A useful range is about 0.05-2.0 moles $H_2SO_4$ per mole of 2,6-dialkyl-4-methoxymethyl phenol. A more preferred amount is about 0.07-1.0 mole $H_2SO_4$ and still more preferably about 0.3-0.7 mole $H_2SO_4$ per mole of 2,6-dialkyl-4-methoxymethyl phenol. A most preferred range is 0.4-0.5 moles $H_2SO_4$ per mole of 2,6-dialkyl-4-methoxymethylphenol.

The reaction will proceed over a wide temperature range. A useful range in which to experiment is about 10°-150° C. A more preferred range is about 20°-100° C. and a most preferred range is 20°-50° C.

The reactor should be fitted to permit distillation of a methanol-containing distillate from the reaction mixture while feeding the 2,6-dialkyl-4-methoxymethylphenol. Depending on reaction temperature, it is usually necessary to lower the reactor pressure to cause the distillation. With a 1,1,1-trichloroethane solvent at 20° C., the solvent/methanol mixture distilled at 100 torr. Solvents having a normal boiling point above about 70° C. are more efficient in removing methanol without co-distilling a large amount of inert solvent.

The distillate removed can be merely discarded and replaced by the solvent being added with the 2,6-dialkyl-4-methoxymethyl phenol solution. Preferably the distillate is treated to remove methanol and then recycled to the reaction mixture. One way to do this is to pass the distillate through an adsorbent which has an affinity for methanol. Zeolites can perform this function. Although both natural and synthetic zeolites can be used, the synthetic zeolites are preferred. The "A" type zeolites are effective, especially type 4A zeolite.

Better results are obtained when the 2,6-dialkyl-4-methoxymethyl phenol is fed to the inert solvent containing the benzene compound and sulfuric acid catalyst over an extended period of time to prevent the accumulation of a large amount of 2,6-dialkyl-4-methoxymethyl phenol in the reaction mixture. Feed time will depend upon scale and rate of methanol removal. A useful time range in which to experiment to optimize results is about 0.5-12 hours. A more preferred feed period is 1-8 hours.

The following example shows the best mode known to the inventors for carrying out the process.

EXAMPLE 1

In a reaction flask fitted with a stirrer, thermometer, pressure equalized addition funnel and a reflux condenser was placed 35 mL of 1,1,1-trichloroethane, 1.17 g of mesitylene and 1.5 g of 95% sulfuric acid. The reflux condenser was constructed such that the condensate was drained down through a tube containing 25 g of activated type 4A zeolite and then returned to the reaction flask. The addition funnel was charged with a solution of 8.37 g of 2,6-di-tert-butyl-4-methoxymethyl phenol in 40 mL of 1,1,1-trichloroethane. The stirred reaction flask was held at 20° C. and the pressure in the system lowered to 100 torr. The 2,6-di-tert-butyl-4-methoxymethyl phenol solution was added dropwise over a 3-hour period while maintaining a steady reflux stream draining through the zeolite bed and back into the reactor. Gas chromatograph analysis showed the reaction mixture excluding solvent to contain:

| | |
|---|---|
| 2,4,6-tri-(3,5-di-tert-butyl-4-hydroxybenzyl) mesitylene | 91.92% |
| 2,4-di-(3,5-di-tert-butyl-4-hydroxybenzyl) mesitylene | 0.80% |
| 4,4'-methylenebis(2,6-di-tert-butyl-phenol) | 7.27% |

Product can be recovered by distilling off part of the solvent and cooling the solution to crystallyze 2,4,6-tri-(3,5-di-tertbutyl-4-hydroxybenzyl) mesitylene.

We claim:

1. A process for making a compound having the structure:

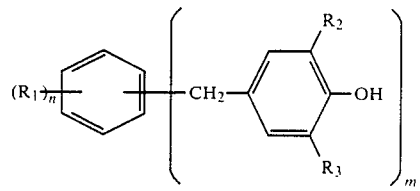

by reacting a reactant having the structure:

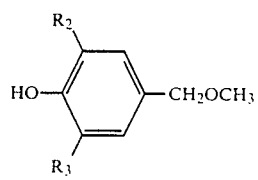

with a benzene compound having the structure:

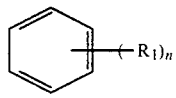

wherein $R_1$ is a $C_{1-3}$ lower alkyl and $R_2$ and $R_3$ are independently selected from the group consisting of $C_{1-8}$ alkyl, $C_{5-8}$ cycloalkyl and $C_{7-12}$ aralkyl, n is zero or an integer from 1 to 4, m is an integer from 2 to 3, and m+n does not exceed 6, in an inert solvent in the presence of sulfuric acid at a temperature of about 20°–150° C. and at a pressure such that methanol by-product formed in the reaction distills out of the reaction mixture as a methanol-containing distillate as it is formed.

2. A process of claim 1 wherein said inert solvent is an aliphatic or aromatic normally liquid halohydrocarbon.

3. A process of claim 2 wherein said benzene compound is durene.

4. A process of claim 3 wherein said reactant is 2,6-di-tert-butyl-4-methoxymethyl phenol.

5. A process of claim 4 wherein said inert solvent is a normally liquid chlorohydrocarbon having a normal boiling range of 40°–200° C.

6. A process of claim 2 wherein said benzene compound is mesitylene.

7. A process of claim 6 wherein said reactant is 2,6-di-tert-butyl-4-methoxymethyl phenol.

8. A process of claim 7 wherein said inert solvent is a normally liquid chlorohydrocarbon having a normal boiling range of about 40°–200° C.

9. A process of claim 7 wherein said inert solvent is a normally liquid chlorohydrocarbon having a normal boiling range of about 50°–150° C.

10. A process for making 2,4,6-tri-(3,5-di-tert-butyl-4-hydroxybenzyl) mesitylene, said process comprising (a) placing a solvent amount of a normally liquid chlorohydrocarbon having a normal boiling range of about 50°–150° C. in a reaction vessel, (b) adding about one mole part of mesitylene to said reaction vessel, (c) adding about 0.25–2.0 moles of $H_2SO_4$ acid to said reaction vessel, (d) feeding about 3–3.6 mole parts of 2,6-ditert-butyl-4-methoxymethyl phenol to said reaction vessel over an extended period of about 0.5–12 hours while maintaining the contents of said reaction vessel at 20°–100° C. and the pressure within said reaction such that methanol formed in the reaction distills out of said reaction vessel as a methanol-containing distillate and (e) recovering said 2,4,6-tri-(3,5-di-tertbutyl-4-hydroxybenzyl) mesitylene product.

11. A process of claim 10 wherein said inert solvent is 1,1,1-trichloroethane or a mixture of trichloroethanes.

12. A process of claim 11 wherein the amount of said concentrated sulfuric acid is about 0.75–2.0 moles.

13. A process of claim 12 wherein said 2,6-di-tertbutyl-4-methoxymethyl phenol is fed as a solution in said inert solvent.

14. A process of claim 1 wherein said methanol-containing distillate is contacted with a zeolite adsorbent having an affinity for methanol thereby removing at least part of the methanol from said methanol-distillate and then recycling the methanol-depleted distillate to the reaction mixture.

15. A process of claim 14 wherein said zeolite is an "A" type zeolite.

16. A process of claim 15 wherein said zeolite is type 4A zeolite.

17. A process of claim 10 wherein said methanol-containing distillate is contacted with a zeolite adsorbent having an affinity for methanol thereby removing at least part of the methanol from said methanol-containing distillate and then recycling the methanol-depleted distillate to the reaction mixture.

18. A process of claim 17 wherein said zeolite is an "A" type zeolite.

19. A process of claim 18 wherein said zeolite is type 4A zeolite.

* * * * *